United States Patent
Daniel et al.

(10) Patent No.: US 6,853,925 B2
(45) Date of Patent: Feb. 8, 2005

(54) GAS FLOW METHOD FOR DETECTION OF LOCAL PREFORM DEFECTS BASED ON STATISTICAL ANALYSIS

(75) Inventors: Isaac M. Daniel, Morton Grove, IL (US); Sun Kyoung Kim, Evanston, IL (US); Jeremy G. Opperer, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 10/611,318

(22) Filed: Jul. 1, 2003

(65) Prior Publication Data

US 2004/0083065 A1 Apr. 29, 2004

Related U.S. Application Data

(60) Provisional application No. 60/394,007, filed on Jul. 3, 2002.

(51) Int. Cl.[7] ............ G06F 19/00; G01N 15/08
(52) U.S. Cl. ............ 702/35; 73/38
(58) Field of Search ............ 702/35; 73/38; 425/127; 264/40.7; 703/7; 700/204

(56) References Cited

U.S. PATENT DOCUMENTS 6,532,799 B2 * 3/2003 Zhang et al. ............ 73/38

OTHER PUBLICATIONS

Sawley et al., Modelling of Flow in Porous Media and Resin Transfer Moulding Using Smoothed Particle Hydrodynamics, Dec. 6–8, 1999, Second International Conference on CFD in the Minerals and Process Industries, Australia.*

Berker et al., Sensor Based Modeling and Control of Fluid Flow in Resin Transfer Molding, Oct. 1998, Journal of Materials Processing & Manufacturing science, vol. 7, pp. 195–214.*

Mathur et al., Optimization of Gate andVent Locations for Resin Infusion Processes Using Genetic Algorithms, Jun. 1998, Proceeding of the American Control Conference, Philadelphia, pp. 2176–2180.*

(List continued on next page.)

*Primary Examiner*—John Barlow
*Assistant Examiner*—Toan M. Le

(57) ABSTRACT

Methods to detect and characterize a defect in a fiber preform residing in a molding cavity for liquid composite molding (e.g. resin transfer molding) to make a composite component or structure. The defect may result from fiber preform misplacement in the molding cavity, accidental inclusions, preform density variations, and/or distortion of the preform. Gas pressures at multiple locations on a mold wall are measured during gas flow through the mold cavity containing the fiber preform. Normalized or measured pressures are analyzed by discriminant analysis to detect and characterize any defect in the tested fiber preform.

11 Claims, 10 Drawing Sheets

OTHER PUBLICATIONS

Sevostianov et al., Mathematical Model of cavitation During Resin Film Infusion Process, 2000, Composite Structures, vol. 48, pp. 197–203.*

Dimension prediction and control for resin transfer molding process; Proceedings of SAMPE Conference; pp. 1–14; May 11–15, 2003; C. Dong et al.

Gas assisted real–time assessment of whole–field permeability profile of fiber preform for liquid composite molding processes; Proceedings of SAMPE Conference; pp. 1–13; May 11–15, 2003; C. Zhang et al.

Optimal control of accelerator concentration of resin transfer molding process; International Journal of Heat and Mass Transfer, vol. 46, pp. 3747–3754, 2003, S.K. Kim et al.

Gas Flow Method for Detecting Local Preform Defects by Inverse Estimation of Space–varying Permeability; Journal of Composite Materials, vol. 37, No. 15, pp. 1367–1383, 2003, S.K. Kim et al.

Determination of three–dimensional permeability of fiber preforms by the inverse parameter estimation technique; Composites: Part A, vol. 34, pp. 421–429, 2003, S.K. Kim et al.

Determination of In–Plane Permeability of Fiber Preforms by the Gas Flow Method Using Pressure Measurements; Polymer Composites, vol. 24, No. 1, pp. 34–44, 2003, S. K. Kim et al.

Determination of permeability of fibrous medium considering inertial effects; Int. Com. Heat Mass Transfer, vol. 29, No. 7, pp. 879–885, 2002, S.K. Kim et al.

Detection of local preform defects by gas flow method and statistical analysis; Advanced Composites Letters; vol. 12, No. 3, pp. 109–114 2003, S. K. Kim et al.

In–Situ quality control of RTM preforms by the gas flow method; 48th International SAMPE Symposium, pp. 1702–1713, May 11–15, 2003.

Solution ot inverse heat conduction problem in nanoscale using sequential method; Numerical Heat Transfer, Part B; vol. 44; pp. 439–456, 2003, S.K. Kim et al.

In–situ measurement and monitoring of fiber preform permeability for liquid composite molding; Proceedings of the 45th International SAMPE Symposium, vol. 45, p. 2053, 2000, Z. Liang et al.

Gas flow method for detection of local preform defects based on statistical analysis; Proceedings of ICCM 14 Conference; pp. 1–8 Jul. 14–18, 2003; S.K. Kim and I.M. Daniel.

New set–up for measurement of permeability properties of fibrous reinforcements for RTM; Composites: Part A, vol. 33, pp. 959–969, 2002, K. Hoes et al.

Permeability Measurement and Flow Simulation Through Fiber Reinforcement; Polymer Composites, vol. 17, No. 1, 34–42, Feb. 1996, R. Gauvin et al.

A control volume finite–element method for two–dimensional fluid flow and heat–transfer; Numerical Heat Transfer, vol. 6, pp. 245–261, 1983, B.R. Baliga et al.

A gas flow method for determination of in–plane permeability of fiber preforms; Polymer Composites, vol. 22, No. 1, pp. 47–56, 2001, M.K. Um et al.

Statistical characteristization of fiber permeability for composite manufacturing; Polymer Composites, vol. 21, No. 6, pp. 996–1006, Dec. 2000, R. Pan et al.

* cited by examiner $$DF^1{}_{km} = 1.991\, P_{1km} - 0.753\, P_{2km} - 0.04\, P_{3km} + 1.402\, P_{4km}$$
$$- 0.537\, P_{5km} + 0.393\, P_{6km} + 5.613\, P_{7km} - 0.995\, P_{8km}$$
$$+ 2.135\, P_{9km} + 2.789\, P_{10km} - 5.848\, P_{11km} + 1.325\, P_{12km} +$$
$$2.964\, P_{13km} + 0.122\, P_{14km} - 0.27\, P_{15km} - 0.371\, P_{16km}$$
$$+ 6.723\, P_{17km} - 2.207\, P_{18km} - 1.752\, P_{19km} - 0.214\, P_{20km}$$
$$- 0.407\, P_{21km} - 1.3\, P_{22km} + 0.605\, P_{23km}$$

GAS FLOW METHOD FOR DETECTION OF LOCAL PREFORM DEFECTS BASED ON STATISTICAL ANALYSIS

This application claims the benefits of provisional application Ser. No. 60/394,007 filed Jul. 3, 2002.

CONTRACTUAL ORIGIN OF THE INVENTION

The United States Government may have rights in this invention pursuant to Contract No. N00014-00-C-0419 between the Office of Naval Research and Northwestern University, Evanston, Ill.

FIELD OF THE INVENTION

The present invention relates to detection and characterization of defects in a fiber preform for use in the liquid molding method for making composite components or structures.

BACKGROUND OF THE INVENTION

The resin transfer molding (RTM) process has become a popular composite manufacturing process due to its suitability for high volume production and cost effectiveness [see references 1, 2]. In this process, the dry fiber reinforcement (preform) is enclosed in the mold and resin is injected and allowed to cure. Resin injection or transferability is defined by the permeability of the preform and it can be severely affected by defects, distortions or anomalies in the preform. In some cases, such as those involving complex geometries, it is not uncommon for the preform to be misplaced or shift and be distorted during mold closure. This fact, if not detected and corrected before resin injection, results in costly scrapping of the finished part [see reference 3]. Preform defects can cause local permeability non-uniformities and affect the resin flow resulting in local resin-starved areas. Furthermore, preform distortions could contribute to residual stresses and undesirable stress concentrations during subsequent loading in service. Thus, detection of preform defects and irregularities is a very important quality control step for reducing costly scrapping and insuring the quality and reliability of fabricated composite structures.

The impregnation of the fluid into the preform is defined by the permeability of the reinforcement, which is the ability of a Newtonian fluid to permeate a porous medium with a sufficiently low Reynolds number, as given by Darcy's Law. The permeability of an undistorted preform with a constant fiber volume ratio can be assumed to be uniform over the entire domain; however, the permeability can be significantly altered by defects, distortions, or other anomalies in the preform. Such drastic changes in local permeability can affect resin flow patterns, rendering portions of the mold to be insufficiently filled. Permeability variations within a preform can be attributed to a number of factors, such as improper preform preparation, misplacement or shifting in the mold, accidental inclusion of foreign material, natural surface density variation of the preform, etc. If such occurrences were not detected prior to resin injection, the potential for costly part scrapping would be increased. Aside from the additional voids due to permeability non-uniformities, preform distortions could contribute to residual stresses and stress concentrations during in-service loading. Early detection, therefore, of such reinforcement irregularities is critical for effective quality control.

Conventional methods for permeability measurement rely on oils or other viscous fluids to be injected into the reinforcement. These fluids soil the fibers and cannot be removed without damage to the preform. Furthermore, the bulk material permeability data obtained from such tests would not provide the information regarding local permeability variation, which is necessary for locating defects. Such strategies, therefore, could not logically be applied in-situ prior to an RTM run. Methods, however, providing multiple pressure measurements with a gas, like the gas flow method, are well suited for such applications.

Published US Patent Application US 2002/0046596 A1 describes a system for in-situ and on-line monitoring of a preform layup process for liquid composite molding using flow of a compressed gas through the preform in the mold cavity. Pressure transducers communicated to openings in a lower mold section provided sensed gas pressure values to a data acquisition and processing device having software which generates a pressure profile of the gas flow for the preform. This pressure profile is evaluated by comparing it with a theoretically calculated pressure profile. The method described in the patent application is inherently one-dimensional and was not proven with preform materials having varying degrees of anisotropy. Furthermore, it requires prior determination of the permeability of the perform material.

SUMMARY OF THE INVENTION

The present invention relates to detection and characterization of a defect in a fiber preform residing in a mold cavity for liquid composite molding (e.g. resin transfer molding) to make a composite component or structure. The defect may result from fiber preform misplacement in the mold cavity, accidental inclusions, preform density variations, and/or distortion of the preform. The method of detecting a defect in a fiber preform residing in a molding cavity involves flowing a gas through the mold cavity containing the fiber preform, measuring gas pressures at multiple locations on a mold wall during gas flow through the mold cavity containing the fiber preform, and analyzing the gas pressures, or results derived therefrom, using discriminant analysis to detect a defect in the fiber preform.

Pursuant to an embodiment of the invention, gas pressures at multiple locations on a mold wall are measured during gas flow through the mold cavity containing the fiber preform. Pressures at the same mold wall locations are obtained by numerical calculation using the control volume finite element method. Then, the measured pressures, which are normalized with respect to the computed pressures, are analyzed in a statistical manner using discriminant analysis (DA), which is based on the multivariate analysis of variance, to determine the uniformity, quality or acceptability of the tested preform. This embodiment of the method is applied to the fiber preforms which can have different types of defects that affect perform quality and thus quality of the molded component. Results derived from the measured and calculated pressure data (e.g. local preform permeability variations) may also be used in practice of the method.

Pursuant to another embodiment of the invention, gas pressures at multiple locations on a mold wall are measured during gas flow through the mold cavity containing the fiber preform. A variety of acquired gas pressure data from different fiber preforms, or results derived from the pressure data (e.g. local preform permeability variations), are grouped by classifications according to existence, location, severity, and type of defect to build up a data base. The acquired or derived data from a fiber perform currently being tested in the mold cavity are analyzed by particular discriminant analysis (DA) that uses the data base and all acquired independent variables together to determine if a defect is present in the fiber perform currently being tested (as a result of the test perform deviating from a previously defined standard, defect-free group) and to predict the membership of the fiber preform being tested into one of the groups of the data base including a standard defect-free group and one or more groups associated with one or more specific types of defects. If a defect is detected, it is further identified by location and severity and type of defect using DA.

Advantages and details of the present invention will be more readily apparent from the following detailed description taken in conjunction with the following drawings.

DESCRIPTION OF THE DRAWINGS

FIG. 7 illustrates discriminant functions 1, 2, and 3 referred to in Table 1 where $P_{1\ km}$, $P_{2\ km}$, $P_{3\ km}$, etc. each represents a normalized measured pressure at a specific pressure tap location (e.g. location 1, 2, 3 etc.) for group k and case (test preform) m with respect to gate (inlet) pressure.

DESCRIPTION OF THE INVENTION

Figure 1:
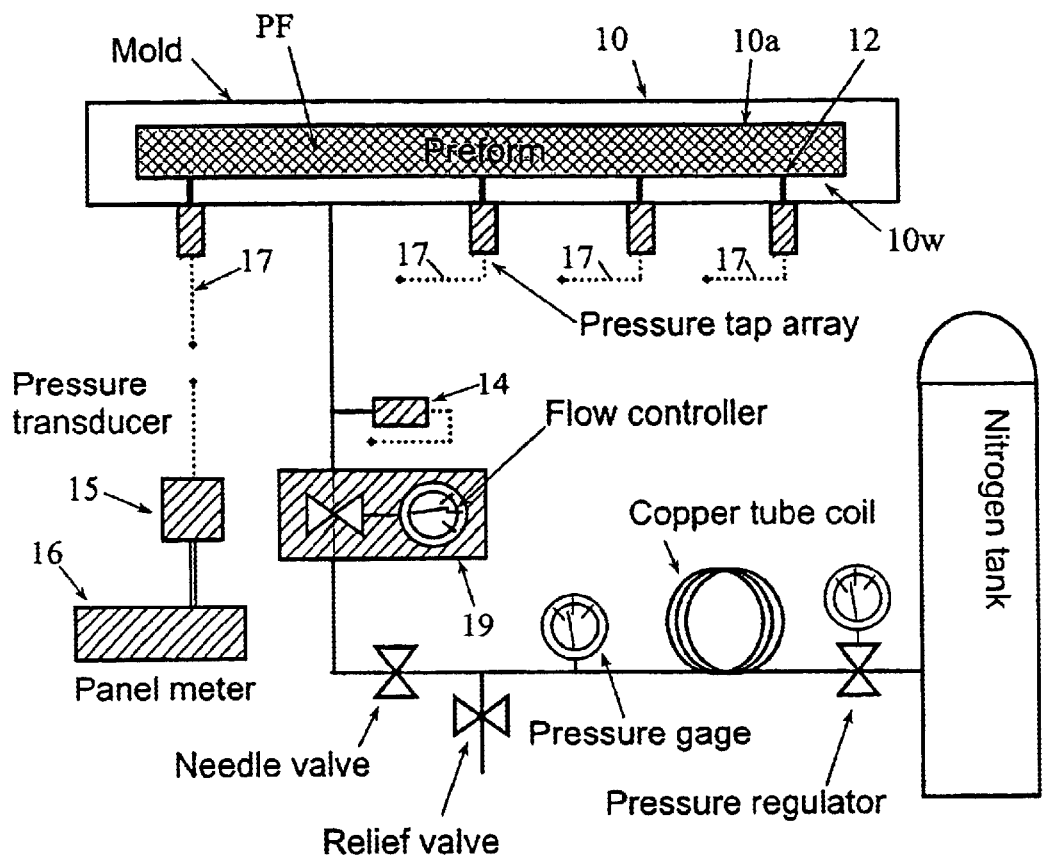
FIG. 1 is a schematic view of apparatus for practicing an embodiment of the invention.

For purposes of illustration and not limitation, the invention will be described with respect to a simulated resin transfer mold 10 shown in FIGS. 1, 1A, and 1B. The simulated resin transfer mold 10 comprised a 229×279×3.17 mm aluminum mold wherein the corners of the rectangular-shaped mold cavity 10a were rounded with 12.7 mm radii. The mold comprised a bottom mold portion 10b, annular middle mold portion 10c, and upper mold portion 10d clamped together using conventional guide pins (not shown) received in aligned holes 10h and eight C-clamps (not shown) evenly spaced about the mold 10. O-ring seals 11a, 11b were disposed between the mold portions as shown in FIG. 1A. The wall 10w of the bottom portion 10a of the mold had twenty-five uniformly spaced 7.94 mm diameter ports 12. FIG. 2 shows a photograph of the bottom mold portion 10b. The middle mold portion 10c constitutes a frame with a cutout in the shape of the desired fiber preform PF to be received in the mold cavity 10a. The upper mold portion 10d is used to compress the fiber preform PF and maintain a predetermined fiber volume ratio. To this end, the upper mold portion 10d includes a lowermost region that fits with close tolerance into the cutout frame (middle portion 10c) to contact the fiber preform.

Figure 1A:
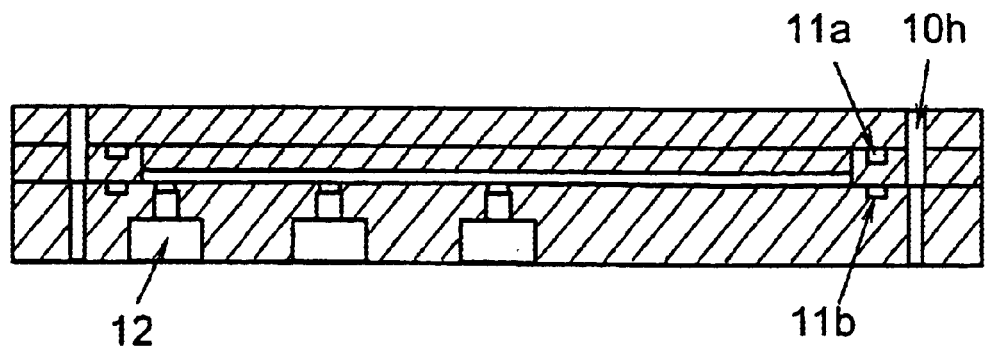
FIG. 1A is a sectional view of the mold.
Figure 1B:
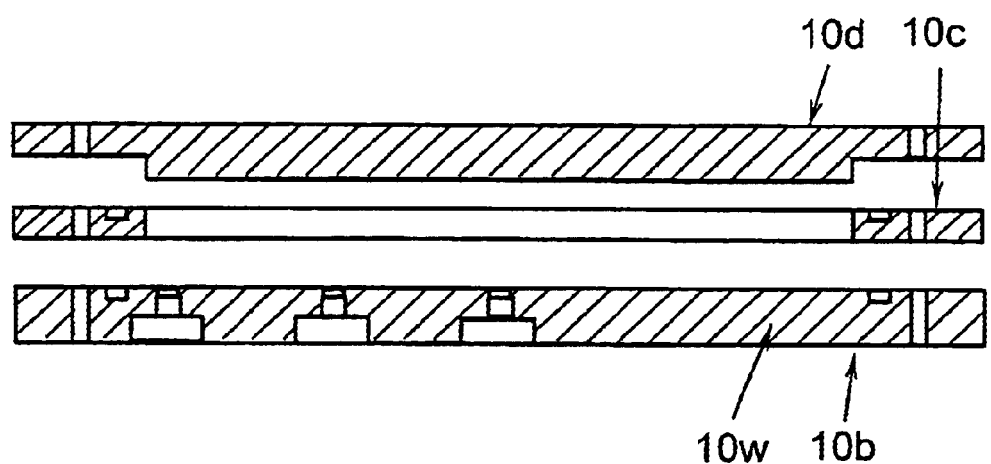
FIG. 1B is an exploded view of the mold.
Figure 2:
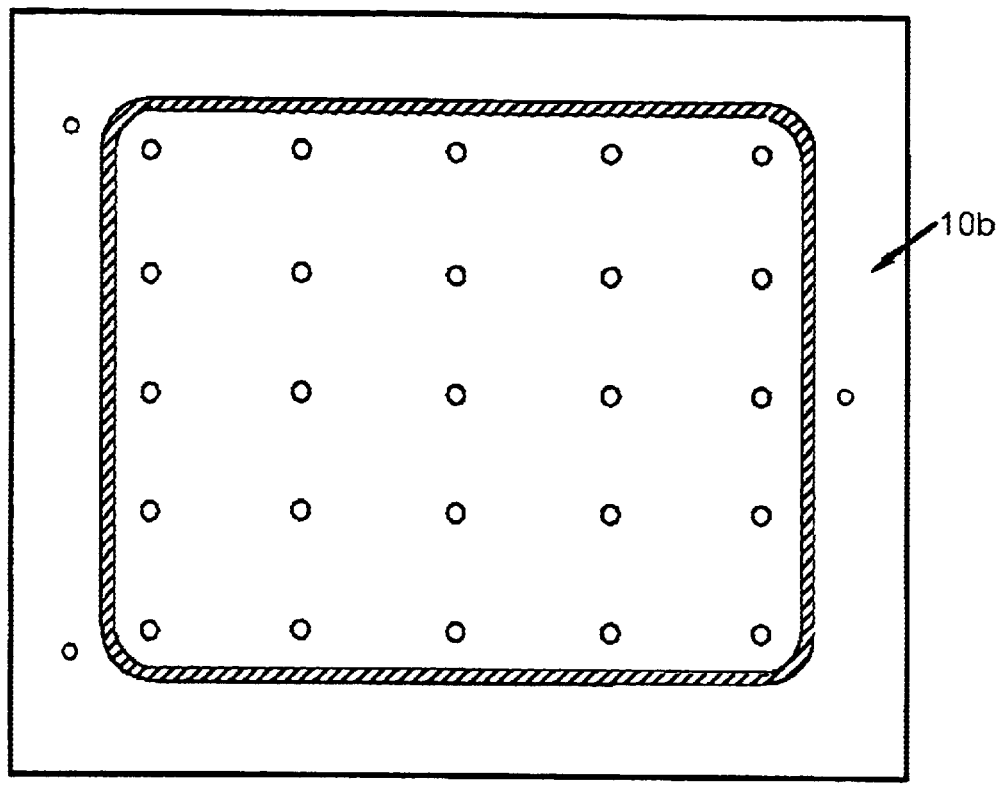
FIG. 2 is a photograph of a bottom part of the mold.

A schematic view of the overall simulated resin transfer mold and associated test components is shown in FIG. 1. Nitrogen gas was used for the experiments as the test gas. A nitrogen tank was employed to provide a constant supply of gas at ambient temperature. The gas was delivered from the tank though a 15 mm tubing coil made of 122 copper alloy. The tubing provides a flexible line to help when positioning equipment, and also ensures that the gas will remain at ambient temperature at the end of the coil. A dial gage shown at the end of the tubing coil was used to monitor the line pressure and maintain it below the maximum capacity of a flow controller 19. The line then continues past a relief valve and onto two control needle valves shown. The flow controller 19 (Omega, FMA-A2401), which ensures constant flow rate, was then used to indicate and regulate the volume flow rate. Immediately prior to entering the mold 10, a pressure tap 14 was installed on the gas line to provide the inlet pressure for the experiment. All ports 12 had female NPT treading to facilitate their use as pressure taps or gates. NPT to barbed fittings and compression fittings were used accordingly. A differential pressure-transducer (Omega, PX278-01D5V) 15 was used to acquire all pressure readings. The gate pressure determined settings for the transducer when applicable. A strain gage panel meter 16 (Omega, DP25-E-A) was used to provide excitation to the transducer and give a digital pressure output. The uncertainty of the pressure measurement with this system was calculated to be 1.04% from the accuracies of the pressure transducer and panel meter 16. The repeatability of the experiments performed using this equipment was considerably high, with negligible variation between tests.

Figure 3:
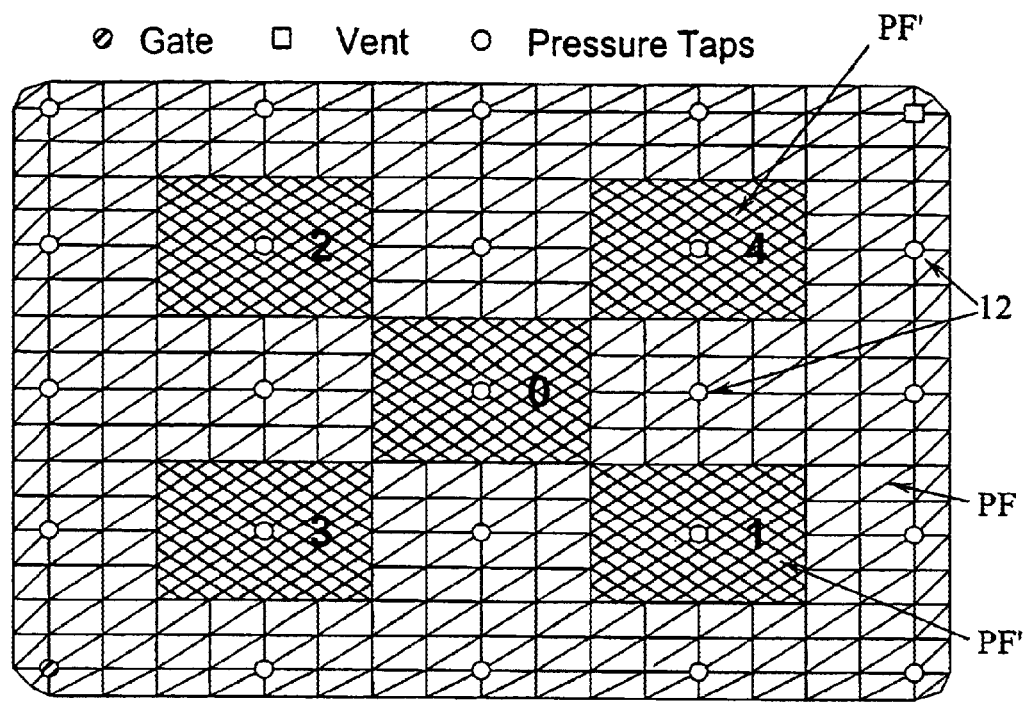
FIG. 3 is a view of mesh and test strategy used for a particular fiber perform in a mold with an array of gas ports.

The locations of the gate for incoming gas and vent for discharging gas on the bottom mold portion 10b are as shown in FIG. 3. The gate was connected to the gas inlet line while the vent was open to the atmosphere. All remaining ports 12 were used as pressure taps. The flow-rate was set with the flow controller. After the desired flow was achieved, pressure measurements were taken at each of the available pressure taps. The pressure transducer, wired to the panel meter, was connected to each of the pressure taps on the mold and on the gas line, one at a time, until all tap pressures were recorded. Measurements were taken by connecting tubing 17 of the tap to the pressure transducer 15 and releasing a shutoff clamp (not shown) on the tubing 17. The shutoff clamp ensured that no flow through the tap was taking place when not in use and provided a negligible pressure drop. Once a tap pressure was recorded, the transducer 15 was disconnected and the shutoff clamp was put back in place. The procedure was then repeated at other pressure taps. Tests were performed for fiber preforms consisting of a random mat fiberglass (OCM8610, 1.5 oz available from Owens Corning). The number of plies used was determined by the desired fiber volume ratio, which was set at 39% in this investigation.

Utilizing the multi-port mold 10, the gate and vent configuration can be selected in a variety of ways: however, in this test, only a diagonal configuration was considered which places both the gate and vent near the ends of a diagonal across the mold cavity 10a as shown in FIG. 3. Small preform patches PF' were placed in the shaded areas shown in FIG. 3 to simulate defects in the preform PF. Two- or six-ply patches PF' at one of five locations were considered in this test. Because of symmetry, data for configurations 1–4 was obtained by simply interchanging gate and vent locations. The patch location and number of plies are denoted by location-patch hereafter. Therefore, 0–2 would designate a case with 2 plies at the center location.

Pursuant to an illustrative embodiment of the invention, a method is provided for detection of a defect in a fiber preform PF residing in a molding cavity 10a of simulated resin transfer mold 10. The method involves measuring gas pressures at multiple locations on a mold wall 10w during gas flow through the mold cavity 10a containing the fiber preform. Pressures at the same mold wall locations (pressure taps) are obtained by numerical calculation using the control volume finite element method, which is described in reference 4 incorporated herein by reference. Then, the measured pressures, which are normalized with respect to the computed pressures, are analyzed in a statistical manner using discriminant analysis (DA), which is based on the multivariate analysis of variance (MANOVA) described in reference 5, to determine the uniformity, quality or acceptability of the tested preform. Alternately, results or data derived from the measured and calculated pressure data (e.g. local preform permeability variation results or data) can also be used in practice of the method. The method was applied to test fiber preforms with different types of defects residing in-situ in the mold cavity 10a.

Formulation

Combining the law of mass conservation, Darcy's law, and the ideal gas law, we obtain the following governing equation for the pressure [see reference 8]

$$\nabla \cdot \left[ \frac{p}{\mu RT} K \nabla p \right] = 0 \quad (1)$$

where R, T, $\mu$, p, and K are the specific gas constant, temperature, pressure, viscosity, and the permeability tensor, respectively. Boundary conditions for the governing equation are as follows, $$p = p_o \text{ at the injection gate, } p = 0 \text{ at air vents,} \quad (2)$$

$$\frac{\partial p}{\partial n} = 0 \text{ along walls}$$

Defects in the preform cause a change in the local fiber volume fraction by limiting the porous nature of the affected unit cells and creating non-Darcy flow regions. This in turn relates to a variance in the local permeability which can be detected as a deviation in the flow rate/pressure gradient relationship as given by Darcy's law. This difference can be noted by measuring the pressure profile at various points along the mold wall.

Consider pressure readings $p_i$ for locations i=1, ..., N, where N is the total number of pressure readings available for one test. Dimensionless pressures at each location can then be defined as $$P_i = p_i/p_0 \quad (3)$$

It is noted that each P is a function of location only for a given temperature, permeability, viscosity, and geometry including gate and vent locations, regardless of gate (inlet) gas pressure $p_0$. The numerical discretization of the computational domain for the solution of Equation 1 was conducted by the control volume finite element method (CVFEM) described in reference 4. A numerical mesh is shown in FIG. 3 for a rectangular preform in a mold with an array of ports to be used interchangeably as gates, vents, or pressure taps.

Once the computed pressures, $\tilde{P}_i$, corresponding to pressure tap locations i have been calculated, they can be normalized by Equation 3. The dimensionless values for $\tilde{P}_i$ and $p_i$ can now be used to obtain a normalized measure of pressure deviation of the form $$\Delta P_i = \frac{P_i - \tilde{P}_i}{\tilde{P}_i} \quad (4)$$

These values, as well as the dimensionless pressures obtained from Equation 3, can now be statistically evaluated with discriminant analysis (DA).

To check if a test preform deviates from the normal, DA was employed for classifying cases into groups. DA is able to determine which variables discriminate between two or more naturally occurring groups. The groups considered in this study were the normal preform group and a number of groups associated with specific types of defects. DA is able to determine which variables are the best predictors of the desired classification, if a stepwise method is utilized. The corresponding discriminant function (DF) for analysis of pressure deviation takes the form $$DF^j = \sum_{i=1}^{N} c_i^j \Delta P_i \quad (5)$$

where $c_i^j$ is the i-th coefficient of the j-th discriminant function. DA automatically determines these coefficients so that the first function provides the best overall discrimination between groups; the second provides the second best, and so on. Furthermore, each function is orthogonal (and uncorrelated) to every other function. The total number of possible functions is equal to the lesser quantity of either the number of groups minus one or the number of variables in the analysis.

For analysis of the normalized measured pressures directly pursuant to another embodiment of the invention (i.e. without the need to consider deviation from a computed normal), the following canonical discriminant function is employed which enters all independent variables together, $$DF_{km} = u_0 + \sum_{i=1}^{N} u_i P_{ikm} \quad (6)$$

where the u's are the canonical coefficients obtained from the solution of a system of simultaneous equations relating the between-groups sums of squares and cross products matrix to the within-groups sums of squares and cross products by an eigenvalue and variable coefficients. The subscripts k and m refer to the groups and cases (individual test preform), respectively. A commercial software package (SPSS) is used to perform the DA and is available from SPSS, Inc. Further details of the DA method are set forth in the Appendix and specifically concerning the inclusion and exclusion of variables in the analysis in references 5 and 9–12.

Pursuant to this other embodiment of the invention, gas pressures at multiple locations (pressure taps 12, FIG. 1) on a mold wall 10w are measured during gas flow through the mold cavity 10a containing the fiber preform PF. A variety of acquired gas pressure data from different fiber preforms are grouped by classifications according to existence, location, severity, and type of defect to build up a data base. The acquired or derived data from a fiber perform PF currently being tested in the mold cavity 10a is analyzed by particular discriminant analysis (DA) that uses the data base and all acquired independent variables together to determine if a defect is present in the fiber perform currently being tested (as a result of the test perform deviating from a previously defined standard, defect-free group) and to predict the membership of the fiber preform being tested into one of several groups including a standard defect-free group and one or more groups associated with one or more specific types of defects. If a defect is identified, it is further identified by location and severity using DA.

Figure 4:
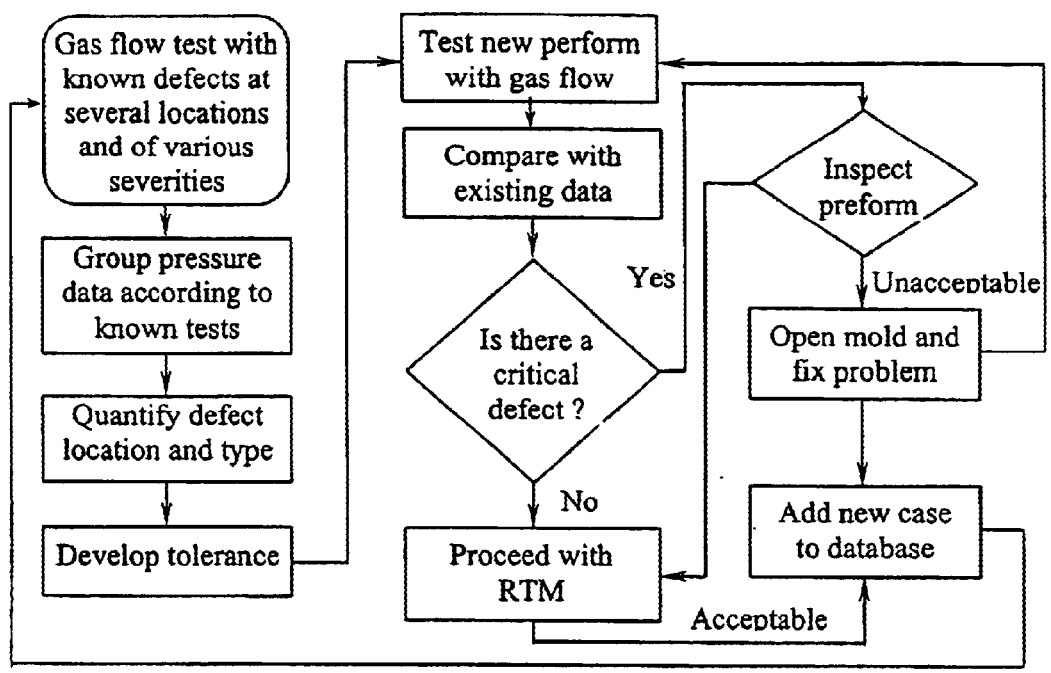
FIG. 4 is a flow chart illustrating application of an embodiment of the gas flow method for performing quality control.
Figure 6:
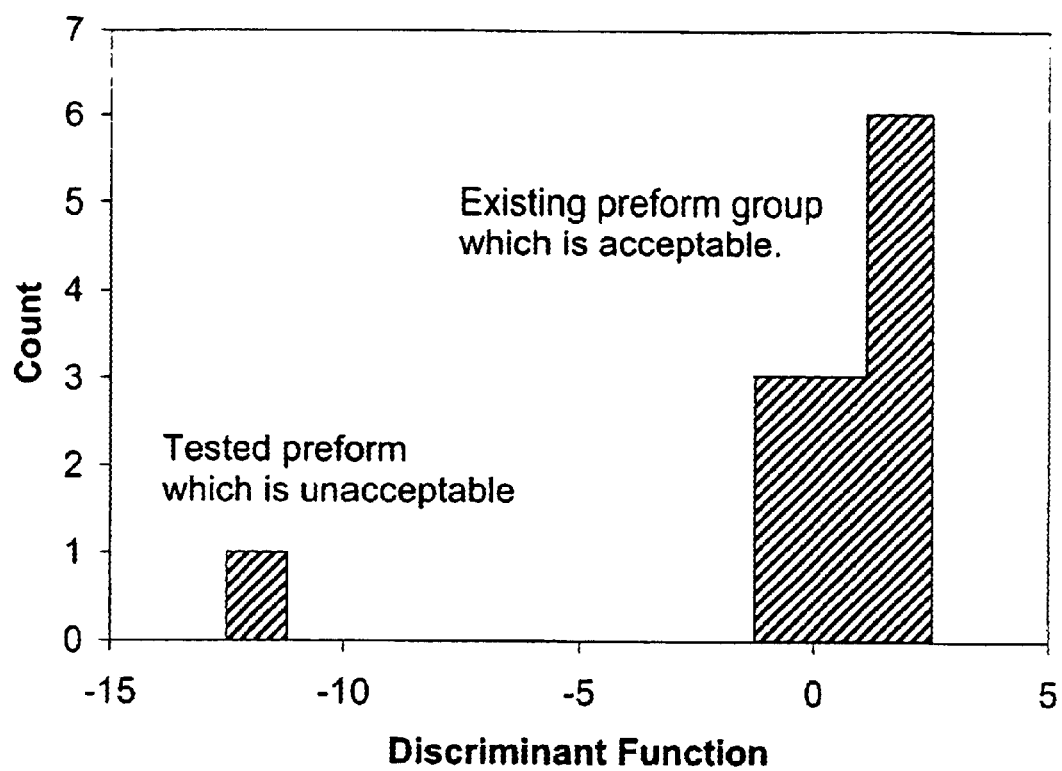

The flowchart of FIG. 4 demonstrates the application of the gas flow method for perform quality control. This method, by which group association from an unidentified perform is accomplished, requires multiple locations of pressure measurement for improved resolution. By minimizing the volume of available pressure data, defect quantification cannot be reliably achieved; however, it may still be possible to detect the general presence of an anomaly. False positive identification can be reduced with the increase of input data per case. Furthermore, the tested mold and perform material must be consistent with those from other tests in order to establish accurate group characterizations. Gate conditions, with regard to either controlled flow or pressure, must also be analogous. Overall, this method can be easily applied with properly located pressure taps.

group data on the DF axis is a measure of the severity of the defect. This is further confirmed by comparing the previous results with those for case 1-6 shown in FIG. 6. Here, the distance between the groups along the axis has increased.

Discriminant analysis can also be used to quantify the defects, with the use of Equation 6. A database is built up of cases assigned to known defect groups. An example of the output generated by the DA software is shown in Table 1. Here, the results have been truncated; only the canonical discriminant scores from the three most revealing functions can be seen. Each case (i.e. test perform) is shown with its original group association. A predicted group membership is then calculated and the probability of the case belonging to the predicted group, given the discriminant score, is also provided. Furthermore, the posterior probabilities and Mahalanobis distances are given. The second most likely group membership is also calculated. As can be seen with case 10, its actual group membership is with 0-0 (0 in the table), however, it is misclassified for the first grouping. The second grouping, however, is correct.

TABLE 1

Truncated screen grab from DA using SPSS 10.0 for Windows

| | | | Highest Group | | | | Second Highest Group | | | | |
|---|---|---|---|---|---|---|---|---|---|---|---|
| Case Number | Actual Group | Predicted Group | $P/D > d_1$ $G = g1$ p | d1 | $PYG = g1$ $D = d_1$ | Squared Mahalanobis Distance to centroid | Group | $PYG = g1$ $D = d_1$ | Squared Mahalanobis Distance to centroid | Function 1 | Function 2 | Function 3 |
| Original 1 | 0 | 0 | .937 | 10 | .995 | 4.220 | 42 | .004 | 11.905 | .723 | −.641 | −.025 |
| 2 | 0 | 0 | .996 | 10 | .995 | 2.005 | 26 | .002 | 10.711 | .919 | −.926 | .402 |
| 3 | 0 | 0 | .400 | 10 | .816 | 10.477 | 32 | .080 | 11.531 | .036 | 1.459 | .276 |
| 4 | 0 | 0 | .701 | 10 | .924 | 7.262 | 32 | .034 | 10.267 | .034 | −1.845 | .620 |
| 5 | 0 | 0 | .278 | 10 | .982 | 12.110 | 22 | .012 | 17.403 | .361 | −1.713 | .817 |
| 6 | 0 | 0 | .679 | 10 | .950 | 7.490 | 32 | .035 | 10.627 | 1.564 | .346 | −.020 |
| 7 | 0 | 0 | .519 | 10 | .977 | 9.136 | 2 | .018 | 14.504 | −1.245 | −1.479 | .917 |
| 8 | 0 | 0 | .949 | 10 | .994 | 3.961 | 2 | .002 | 13.333 | .251 | −.182 | .083 |
| 9 | 0 | 0 | .782 | 10 | .976 | 6.390 | 2 | .009 | 13.060 | .461 | −.010 | −1.266 |
| 10 | 0 | 26* | .566 | 10 | .722 | 8.651 | 0 | .267 | 14.224 | 1.690 | −3.413 | 1.376 |
| 11 | 0 | 0 | .972 | 10 | .890 | 3.352 | 12 | .004 | 11.029 | .042 | −.066 | .105 |
| 50 | 12 | 12 | .824 | 10 | 1.000 | 5.897 | 16 | .000 | 21.803 | −.467 | 2.287 | −2.980 |
| 51 | 12 | 12 | .817 | 10 | .868 | 5.976 | 0 | .020 | 17.299 | −.104 | 2.677 | −.022 |
| 52 | 22 | 22 | .003 | 10 | 1.000 | 26.649 | 0 | .000 | 55.993 | −.509 | −.915 | 1.564 |
| 53 | 22 | 22 | .846 | 10 | .819 | 5.623 | 0 | .366 | 10.255 | −1.009 | −1.886 | 1.114 |

Test Results and Discussion

Figure 5:
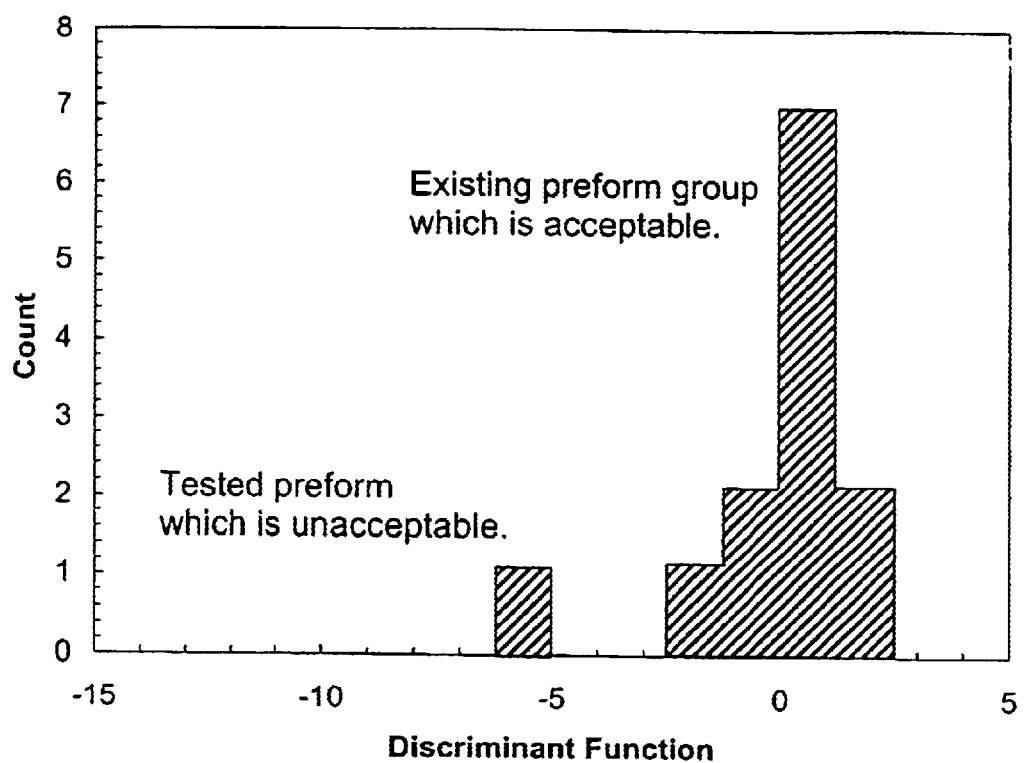
FIGS. 5 and 6 are results of discriminant analysis for test preforms 1–2 and 1–6, respectively.
Figure 7:
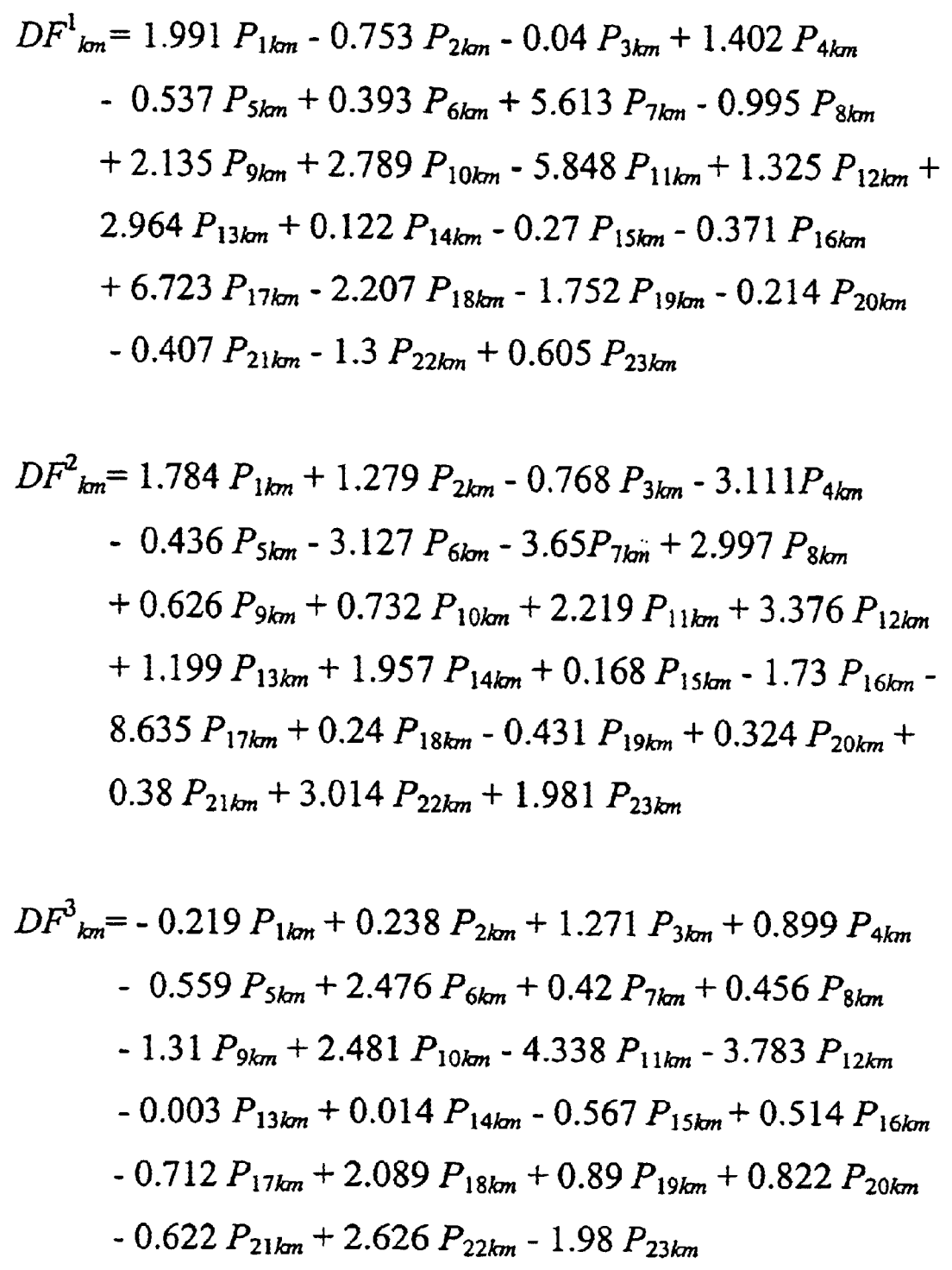

Pressure data acquired for each case is normalized according to Equation 3 and then categorized according to flaw characterization, flaw data, and preform type (if another preform has been tested). Equation 4 can then be employed to analyze data compared against the computed pressures. FIG. 5 shows results of the DA for case 1-2, where a two ply patch has been added to the perform at location 1. Equation 5 was used to obtain the discriminant scores seen in the figure. The histogram of FIG. 5 shows that the two groups (the normal one and one with a 1-2 defect) have different values of the DF (discriminant function) and are distinct. The relative distance between the test group and reference Functions 1, 2, and 3 are represented in FIG. 7 where $P_1$ km, $P_{2\ km}$, $P_{3\ km}$, etc. each represents a normalized measured pressure at a specific pressure tap location (e.g. location 1, 2, 3 etc.) for group k and case (test preform) m with respect to gate (inlet) pressure.

Figure 8:
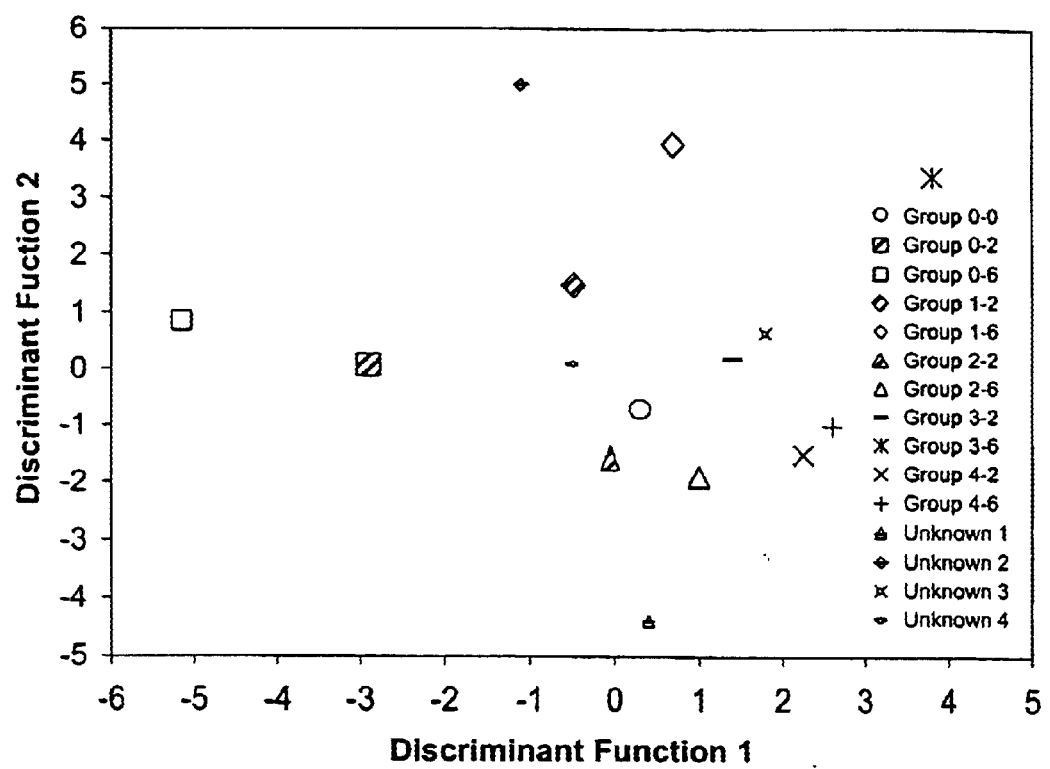
FIG. 8 is a plot of canonical discriminant function scores for unknown defects (unk1, unk2, etc.) and group centroids (group 0—0, 0—2, etc.) plotted with the centroids of the various groups for the first two DF axes.
Figure 9:
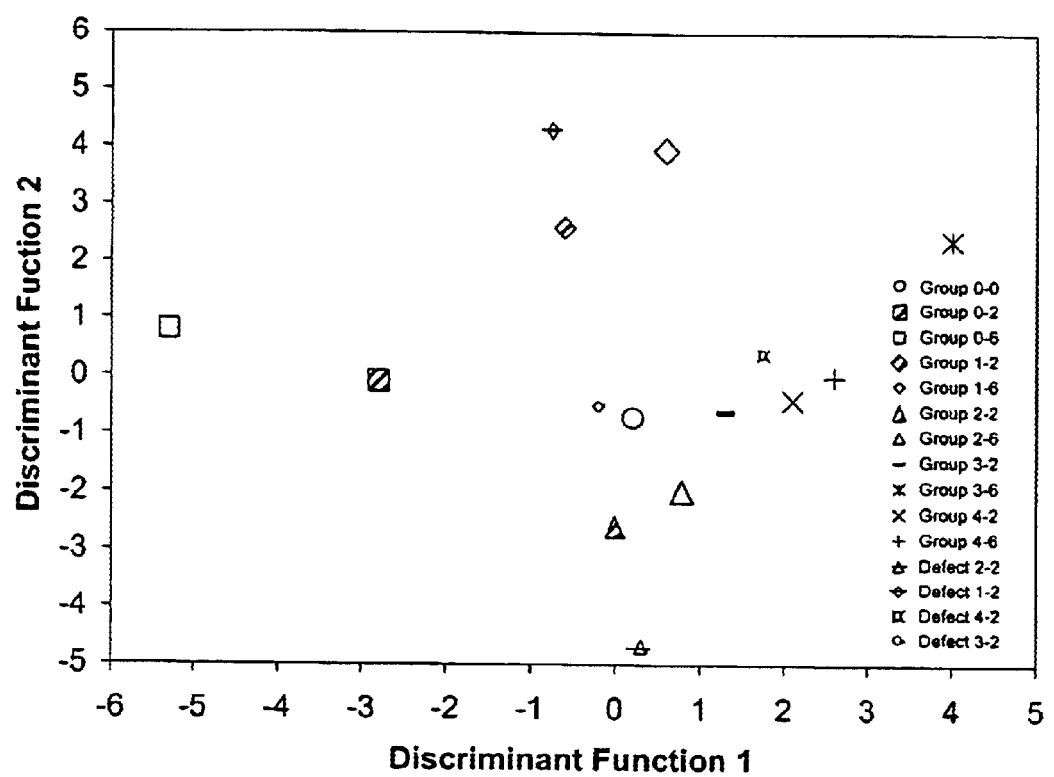
FIG. 9 is a plot of the canonical discriminant function scores for unknown defects, after they have been classified and new canonical discriminant functions have been generated, (e.g. defect 2—2, etc.) plotted with the new centroids of the various groups for the first two DF axes.

The use of this statistical technique has proven to be successful in correctly identifying unknown defects. Discriminant analysis was performed with the existing database and an additional four unclassified cases. These cases were obtained by four experiments with a randomly placed defect of unknown severity by a member outside this research group. The task was then to identify each of these. Each case was successfully identified with the following posterior probabilities: case 2-2, 88.8%, case 1-2, 90.9%, case 4-2, 87.9%, and case 3-2, 73.6%. FIG. 8 shows the canonical discriminant scores for the unknown defects plotted with the centroids for the various groups on the first two DF axes. After each of the unknown defects has been correctly identified, they can be added to the DA database in their respective groups. Once this is done DA can be performed again, and the resulting posterior probabilities are: case 2-2, 99.8%, case 1-2, 100%, case 4-2, 99.9%, and case 3-2, 99.9%. The reason for the increase is that there are new canonical discriminant functions to accommodate the additional data, and therefore, the resulting values will be significantly improved. FIG. 9 shows the scores for the unknown defects, after they have been classified and new canonical discriminant functions have been generated, plotted with the new centroids for the various groups on the first two DF axes.

Data from new tests can be qualified by employing the selected canonical discriminant functions. Usually, only the first three are required to account for the bulk of the variance, at least 75%. The results can be plotted along with the group centroids from the previously established cases. The relative proximity of the new case based on discriminant scores in n-space can be used to identify its group membership. Actual posterior probabilities can then be calculated.

Embodiments of the invention thus were effective in detecting defects occurring during preform placement in the mold by analyzing pressure data obtained during gas flow. Computed pressure deviations can be used to indicate the presence and severity of a defect, while, normalized pressure data can be employed to classify the anomaly. The computed pressures were obtained by a simple numerical analysis. The statistical method is employed to classify test preforms into normal and defective groups. The method was successfully applied to the detection and quantification of defects introduced in the tested preforms using the discriminant analysis (DA) method.

Appendix

With respect to equation (6) set forth above, the canonical discriminant functions used in the analysis are defined as $$DF_{km} = u_0 + \sum_{i=1}^{N} u_i P_{ikm} \tag{A-1}$$

where the $u_i$'s are the canonical coefficients, and $u_0$ is a constant used with the unstandardized coefficients when indicating the absolute contribution of a variable. The subscripts k and m refer to the groups and cases respectively, i.e., DF24 would be the canonical function for case 4 in group 2. The coefficients can be obtained from the solution of a system of simultaneous equations relating the between-groups sums of squares and cross products matrix, B, to the within-group matrix of sums of squares and cross products, W, by an eigenvalue and variable coefficients. Components of the W matrix are obtained from the following equation, $$w_{ij} = \sum_{k=1}^{g} \sum_{m=1}^{c_k} (P_{ikm} - \overline{P}_{ik})(P_{jkm} - \overline{P}_{jk}) \tag{A-2}$$

where g, $c_k$, and $\overline{P}_{ik}$ are the total number of groups, the cases per given group k, and the mean value of pressure at i for all cases in group k, respectively. The index j is used as well to indicate pressure reading location. Components of B can then be calculated by $$b_{ij} + w_{ij} = \sum_{k=1}^{g} \sum_{m=1}^{c_k} (P_{ikm} - \overline{P}_i)(P_{jkm} - \overline{P}_j) \tag{A-3}$$

such that $\overline{P}_i$ is the total mean value of pressure at i for all cases in every group.

Development of the canonical discriminant function is described in more detail in published discriminant analysis texts such as references 9–12. The total number of possible functions is equal to the lesser quantity of either the number of groups minus one or the number of variables in the analysis. Each function maximizes group differences more than those subsequently derived. Furthermore, each function is orthogonal (and uncorrelated) to every other function. The first function provides the largest variation. The second function gives the greatest part of the remaining unexplained variation, and so on.

Group membership classification is achieved through the use of several tools. Discriminant function analysis requires the use of canonical discriminant scores as one means of assigning group membership. These scores can be plotted on axes in n-space. Mahalanobis' squared distance from a case point P to the group centroid k in this space can then be obtained by $$D^2(P|G_k) = (t-g)\sum_{i=1}^{N}\sum_{j=1}^{N} a_{ij}(P_i - \overline{P}_{ik})(P_j - \overline{P}_{jk}) \tag{A-4}$$

where t, g, and $a_{ij}$ are the total number of cases, number of groups, and elements from the inverse W-matrix, respectively. This distance can be measured in terms of chi-square units, $\chi^2$, relates how two of a are different based on the canonical discriminant functions as described in references 10, 12. The smaller the Mahalanobis distance to a given group, the greater the probability of its association with that group, so long as each group demonstrates a multivariate normal distribution [reference 11]. This can then be used to establish a posterior probability $$Pr(G_k|P) = \frac{Pr(P|G_k)}{\sum_{i=1}^{g} Pr(P|G_i)} \tag{A-5}$$

such that the probabilities $Pr(G_k|P)$ and $Pr(P|G_k)$ are defined as the probability that a case belongs to a particular group and the probability that a number of cases are further from the centroid than the tested case, respectively. The aforementioned commercial software package (SPSS) is employed to perform the DA.

Although the invention has been described above in connection with certain embodiments thereof, those skilled in the art will appreciate that various changes, modifications, and the like can be made therein without departing form the spirit and scope of the invention as set forth in the appended claims.

References

The teachings of the following references are incorporated herein by reference:

1. Potter, K., *Resin Transfer Moulding*. 1997, London, UK: Chapman and Hall.
2. Hoes, K., et al., *New set-up for measurement of permeability properties of fibrous reinforcements for RTM*. Composites Part a-Applied Science and Manufacturing, 2002. 33(7): p. 959–969.
3. Gauvin, R., et al., *Permeability measurement and flow simulation through fiber reinforcement*. Polymer Composites, 1996. 17(1): p. 34–42.

4. Baliga, B. R. and S. V. Patankar, *A Control Volume Finite-Element Method for Two-Dimensional Fluid Flow and Heat Transfer*. Numerical Heat Transfer, 1983. 3: p. 245–261.
5. Huberty, C. J., *Applied Discriminant Analysis*. 1994: Wiley-Interscience.
6. Liang, Z., et al. *In-Situ Measurement and Monitoring of Fiber Preform Permeability for Liquid Composite Molding*. in *Proceedings of the* 45th International SAMPE Symposium, Vol. 45(2000) - *"Bridging the Centuries with SAMPE's Materials and Processes"*. 2000. Long Beach, Calif.: SAMPE publishing.
7. Um, M. K., I. M. Daniel, and B. W. Childs, *A gas flow method for determination of in-plane permeability of fiber preforms*. Polymer Composites, 2001. 22(1): p. 47–56.
8. Scheidegger, A. E., *The Physics of Flow Through Porous Media* 3rd ed. 1974, Toronto: University of Toronto Press.
9. Norusis, M. J. and C. M. Wang, *Discriminant*, in *SPSSX Statistical Algorithms*. 1983, SPSS, Inc.: Chicago. p. 79–93.
10. Sachs, L., *Statistical Decision Techniques*, in *Applied Statistics: A Handbook of Techniqeus*. 1984, Springer-Verlag: New York. p. 139–153.
11. Klecka, W. R., *Discriminant Analysis*. 1980, Beverly Hills: Sage Publications. 71.
12. George, D. and P. Mallery, *Discriminant Analysis*, in *SPSS for Windows Step by Step*. 2001, Allyn and Bacon: Boston. p. 264–278.

What is claimed is:

1. A method of detecting a defect in a fiber preform residing in a molding cavity, comprising flowing a gas through the mold cavity containing the fiber preform, measuring gas pressures at multiple locations on a mold wall during gas flow through the mold cavity containing the fiber preform, and analyzing the gas pressures, or results derived therefrom, using discriminant analysis to detect a defect in the fiber preform.

2. A method of detecting a defect in a fiber preform residing in a molding cavity, comprising flowing a gas through the mold cavity containing the fiber preform, measuring gas pressures at multiple locations on a mold wall during gas flow through the mold cavity containing the fiber preform, calculating gas pressures at the same mold wall locations, normalizing the measured pressures with respect to the calculated pressures to provide normalized pressure data, and analyzing the normalized pressure data, or results derived from the measured and calculated gas pressures, using discriminant analysis to detect a defect in the fiber preform.

3. The method of claim 2 wherein the calculating of the pressures at the mold location is conducted by control volume finite element analysis.

4. The method of claim 2 wherein the discriminant analysis is conducted by multivariate analysis of variance.

5. The method of claim 2 wherein the discriminant analysis is conducted using the following canonical discriminant function:

$$DF^j = \sum_{i=1}^{N} c_i^j \Delta P_i \tag{5}$$

where $c_i^j$ is the i-th coefficient for the j-th discriminant function and $\Delta P_i$ is a normalized measure of pressure deviation.

6. A method of detecting and characterizing a defect in a fiber preform residing in a molding cavity, comprising flowing a gas through the mold cavity containing the fiber preform, measuring gas pressures at multiple locations on a mold wall during gas flow through the mold cavity containing the fiber preform, and analyzing the measured pressures, or results derived therefrom, to determine membership of the fiber perform in one of two or more groups that include a standard defect-free group and a defective group, whereby the method determines if the fiber preform deviates from the standard defect-free group.

7. The method of claim 6 wherein the defective group is associated with a specific type of defect.

8. The method of claim 6 wherein the analyzing of the measured pressures, or the results derived therefrom, is conducted by discriminant analysis using a data base generated from previous tests of fiber performs wherein the fiber performs have been grouped by existence, location, severity, and type of defect thereof.

9. The method of claim 6 wherein said results comprise local permeability variation results determined from the measured pressures.

10. The method of claim 6 wherein the following canonical discriminant function is employed which enters all independent variables together, $$DF_{km} = u_0 + \sum_{i=1}^{N} u_i P_{ikm} \tag{6}$$

where the u's are the canonical coefficients obtained from the solution of a system of simultaneous equations relating the between-groups sums of squares and cross products matrix to the within-groups sums of squares and cross products by an eigenvalue and variable coefficients, and wherein the subscripts k and m refer to the groups and test preforms, respectively.

11. The method of claim 6 including determining location and severity of any defect detected.

* * * * *